(12) United States Patent
Paye

(10) Patent No.: US 6,774,096 B1
(45) Date of Patent: Aug. 10, 2004

(54) ZINC OXIDE CONTAINING SURFACTANT SOLUTION

(75) Inventor: Marc Paye, Hognoul (BE)

(73) Assignee: Colgate-Palmolive Co., Piscataway, NJ (US)

(*) Notice: Subject to any disclaimer, the term of this patent is extended or adjusted under 35 U.S.C. 154(b) by 19 days.

(21) Appl. No.: 10/681,935

(22) Filed: Oct. 9, 2003

(51) Int. Cl.$^7$ ................................. A61K 7/50
(52) U.S. Cl. ................ 510/130; 510/139; 510/158; 510/424; 510/426; 510/470; 510/499; 510/503; 510/508
(58) Field of Search ................ 510/130, 139, 510/158, 424, 426, 470, 499, 503, 508

(56) References Cited

U.S. PATENT DOCUMENTS

2002/0010114 A1 * 1/2002 Dufay et al. ............. 510/130
2003/0150064 A1 * 8/2003 Nickel et al. ............. 8/115.51

* cited by examiner

Primary Examiner—Necholus Ogden
(74) Attorney, Agent, or Firm—Richard E. Nanfeldt

(57) ABSTRACT

A cleaning composition for all purpose cleaners, light duty liquids, shampoos such as hair cleaning, foam baths, liquid hand soaps, and shower gels which comprises approximately by weight:

(a) 1% to 50%, more preferably 2% to 40% of at least one surfactant selected from the group consisting of sulfonated anionic surfactants, sulfated anionic surfactants, zwitterionic surfactants, $C_{12}$–$C_{14}$ alkanol amide surfactants, amine oxide surfactants, ethoxylated nonionic surfactants, ethoxylated/propoxylated nonionic surfactants and alkyl polyglucoside surfactants and mixtures thereof;

(b) 0.5% to 10%, more preferably 1% to 8% of at least one solubilizer;

(c) 0.01% to 1%, more preferably 0.03% to 0.5% of Nano-particulates of zinc oxide which function as an anti-irritant system for the surfactants; and (d) the balance being water.

5 Claims, No Drawings

ZINC OXIDE CONTAINING SURFACTANT SOLUTION

FIELD OF INVENTION

This invention relates to the use of a zinc oxide suspension in a surfactant-based product to reduce its skin irritation potential and optimize its compatibility with the skin. The surfactant-based product may be a hand dishwashing liquid, a liquid skin cleanser or any type of cleaning or cleansing product based on surfactants. The particularity of the zinc oxide suspension to decrease the skin irritation potential is to be highly effective even in already optimized surfactant-based product containing other types of counter-irritants such as amphoteric or nonionic secondary surfactants.

BACKGROUND OF THE INVENTION

The present invention relates to the use of zinc oxide particles in light duty liquid detergent compositions with high foaming properties, which can contain mixtures of anionic surfactants, amine oxide surfactant and alkyl polyglucoside surfactant, in order to decrease its skin irritabon potential and improve its skin compatibility.

No prior art related to the use of zinc oxide suspensions in surfactant-based products to decrease the irritation potential of the anionic surfactant have been found.

Zinc oxide suspension is used for other purposes or in other types of products as shown in the following patents. US5403506 describes a deodorant detergent composition containing as a deodorizing component a minor amount of zinc oxide having a particulate size no greater than about 10 microns. KR9300782 describes a soap composition containing metal oxide and ethyl alcohol. FR19750007063 and 19750306 describe the use of zinc oxide to prepare an opaque cleaning composition in tablet form. EP20000902097 and 20000204 describe a process using ultrafine particulate zinc oxide that has a low coagulation of primary particles and can be easily dispersed or suspended in a aqueous solvent without passing through a grinding process, that provides a cosmetic material with transparency and ultraviolet shielding ability. US19960590736 and 19960124 describe a deodorant soap or detergent composition containing a zinc compound and a polyamine. IE 19750000469 and 19750305 describe zinc oxide-containing detergent bars. US19990332007 describes photoprotective cosmetic compositions containing a metal oxide nanopigment, which may be zinc oxide, and an acrylic terpolymer, and the use of these compositions for protecting keratinous material against ultraviolet radiation. WO1997EP00714 and 19970213 describe compositions containing an antifungal and a sulfur compounds for body and hair cleaning products. EP00902097.5 (WO0046152 request) describes cosmetic products containing ultrafine particulates of zinc oxide and the process to formulate them. WOEP0011713 describes a drug-tape composition containing zinc oxide. WOUS0140234 describes skin protective formulations with micronized zinc oxide that allow to reduce skin damages due to light and sun exposure. WOIB0100717 describes a skin protective aerosol composition containing zinc oxide to protect baby bottom from erythema. WOGB0101949 describes the use of zinc oxide as a biostatic agent. WOFR0200046 describes the use of zinc oxide as mineral filter for UV in cosmetic compositions. EP00907548.2 (WO0050503 request) describes redispersible gels with zinc oxide nanoparticles.

Zinc oxide is also used in cosmetic products for the following purposes: zinc oxide may be found in facial masks to absorb excess of sebum (Ella Baché); zinc oxide may be found in Baby Balsam or cream to protect skin from redness in the diaper area (Weleda, Calidou, Mustela); zinc oxide may be found in Skin scrubbing products for its skin lightening properties (Ella Baché); zinc oxide may be used for its astringent and antiseptic properties in drugs and cosmetic products, as well as for its UV A and B radiation blocking effect.

Some publications describing the role of zinc oxide are hereafter: Lansdown AB. Influence of zinc oxide in the closure of open skin wounds. Intl J Cosmet Sci 15: 83–85 (1993). This paper shows that zinc oxide offers potential benefits in skin wound healing; Fairhurst D. Zinc Oxide. Soap Perfum Cosmet 72: 36–37 (1999). This paper describes the beneficial role of zinc oxide in protecting skin from UV A.; Lansdown AB. Zinc and titanium oxides: promising UV-absorbers but what influence do they have on the intact skin ? Intl J Cosmet Sci 19: 167–172 (1997). This paper describes percutaneous absorption of microfine zinc oxide with the influence of its vehicle. Prevedello M. Biochemical interactions of metallic ions in make-up with the skin. SOFW 128: 66–68 (2002). This paper reviews the use of metallic ions in make-up and says that zinc oxide is recommended in order to prevent and heal minor skin disorders as well as to treat the delicate baby skin. Hayashi S et al. The relationship between UVB screening and cytoprotection by microcorpuscular zinc oxide or ascorbate against DNA photodamage and membrane injuries in keratinocytes by oxidative stress. J Photochem Photobiol B 64: 27–35 (2001). This paper describes that microcorpuscular zinc oxide is thought to be cytoprotective through reduction of reactive oxygen species generation, cyclobutane-type pyrimidine dimmers formation and cell membrane disintegration. Baldwin S et al. Skin benefits from continuous topical administration of a zinc oxide/petrolatum formulation by a novel disposable diaper. J Eur Acad Dermatol Venereol 15 (Suppl 1): 5–11 (2001). In the paper, human skin is exposed to the formulation prior to an irritating challenge with SLS and shows a 3.5×reduction in skin barrier damage and skin erythema.

SUMMARY OF THE INVENTION

It has now been found that a light duty liquid detergent can be formulated with a mixture of surfactants and nanoparticulates of zinc oxide in the size of 10–30 nm.

The addition of the zinc oxide particulates does not incur a detriment to grease cleaning efficacy of the dishwashing liquid nor to the foaming properties of the finished product. The skin irritation potential of the finished is highly improved by the presence of the zinc oxide suspension in the product.

As compared to the same product without zinc oxide, the zinc oxide-containing product induces much less erythematous reaction and skin barrier alteration when the products are in contact with the skin for a long period. Benefits in terms of less skin drying and better respect of skin surface hydration are also expected when adding nanoparticles of zinc oxide in the product. Similar anti-irritant effects are also expected in any type of surfactant-based product.

One object of this invention is to provide a light duty liquid detergent composition which comprises a sulfate surfactant, a sulfonate anionic surfactant, an alkyl polyglucoside surfactant, nanoparticulates of zinc oxide having a particle size of 10–30 nm and water.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE INVENTION

A cleaning composition for all purpose cleaners, light duty liquids, shampoos such as hair cleaning, foam baths, liquid hand soaps, and shower gels which comprises approximately by weight:

(a) 1% to 50%, more preferably 2% to 40% of at least one surfactant selected from the group consisting of sulfonated anionic surfactants, sulfated anionic surfactants, zwitterionic surfactants, $C_{12}$–$C_{14}$ alkanol amide surfactants, amine oxide surfactants, ethoxylated nonionic surfactants, ethoxylated/propoxylated nonionic surfactants and alkyl polyglucoside surfactants and mixtures thereof;

(b) 0.5% to 10%, more preferably 1% to 8% of at least one solubilizer;

(c) 0.01% to 1%, more preferably 0.03% to 0.5% of Nano-particulates of zinc oxide which function as an anti-irritant system for the one or more surfactants; and (d) the balance being water.

A preferred light duty liquid compositions of the instant invention comprises approximately by weight:

(a) 2% to 12%, more preferably 3% to 10% of an alkali metal or ammonium salt of a $C_{8-18}$ ethoxylated alkyl ether sulfate surfactant and/or an $C_{8-18}$ alkyl ether sulfate surfactant;

(b) 10% to 30%, more preferably 10% to 20% of an alkali metal and/or alkaline earth metal salt of an anionic sulfonate surfactant;

(c) 0.5% to 10%, more preferably 5% to 10% of an alkyl polyglucoside surfactant;

(d) 0.5% to 10% of at least one solubilizer;

(e) 1% to 12% of an amine oxide surfactant;

(f) 0.01% to 1%, more preferably 0.03% to 0.5% of Nanoparticulates of zinc oxide which functions as an anti-irritant system for anionic surfactants, (g) 0 to 4%, more preferably 0.1% to 4% of a magnesium inorganic salt;

(h) the balance being water.

The anionic sulfonate surfactants which may be used in the instant composition of this invention are water soluble and include the magnesium sodium, potassium, ammonium and ethanolammonium salts of linear $C_8$–$C_{16}$ alkyl benzene sulfonates; $C_{10}$–$C_{20}$ paraffin sulfonates, alpha olefin sulfonates containing about 10–24 carbon atoms and $C_8$–$C_{18}$ alkyl sulfates and mixtures thereof. The preferred anionic sulfonate surfactant is a $C_{12-18}$ paraffin sulfonate.

The paraffin sulfonates may be monosulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14-17}$ range will be minor and will be minimized, as will be any contents of di- or poly-sulfonates.

Examples of suitable other sulfonated anionic detergents are the well known higher alkyl mononuclear aromatic sulfonates, such as the higher alkylbenzene sulfonates containing 9 to 18 or preferably 9 to 16 carbon atoms in the higher alkyl group in a straight or branched chain, or $C_{8-15}$ alkyl toluene sulfonates. A preferred alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Preferred materials are set forth in U.S. Pat. No. 3,320,174, especially those in which the alkyls are of 10 to 13 carbon atoms.

The $C_{8-18}$ ethoxylated alkyl ether sulfate surfactants have the structure

$$R\text{—}(OCHCH_2)_n OSO_3^{M^+}$$

wherein n is about 1 to about 22 more preferably 1 to 3 and R is an alkyl group having about 8 to about 18 carbon atoms, more preferably 12 to 15 and natural cuts, for example, $C_{12-14}$ or $C_{12-16}$ and M is an ammonium cation or a metal cation, most preferably sodium.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3 EO) sulfate.

Ethoxylated $C_{8-18}$ alkylphenyl ether sulfates containing from 2 to 6 moles of ethylene oxide in the molecule are also suitable for use in the invention compositions. These detergents can be prepared by reacting an alkyl phenol with 2 to 6 moles of ethylene oxide and sulfating and neutralizing the resultant ethoxylated alkylphenol.

The amine oxide semi-polar nonionic surfactants used in the instant compositions comprise compounds and mixtures of compounds having the formula

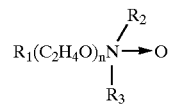

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

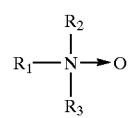

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 which is hereby incorporated herein by reference.

The alkyl polysaccharides surfactants, which are used in conjunction with the aforementioned surfactants have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula

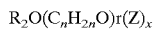

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol (R$_2$OH) can be reacted with glucose, in the presence of an acid catalyst to form the desired glucoside. Alternatively the alkyl polyglucosides can be prepared by a two step procedure in which a short chain alcohol (R$_1$OH) can be reacted with glucose, in the presence of an acid catalyst to form the desired glucoside. Alternatively the alkyl polyglucosides can be prepared by a two step procedure in which a short chain alcohol (C$_{1-6}$) is reacted with glucose or a polyglucoside (x=2 to 4) to yield a short chain alkyl glucoside (x=1 to 4) which can in turn be reacted with a longer chain alcohol (R$_2$OH) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

wherein n=10 (2%); n=122 (65%); n=14 (21–28%); n=16 (4–8%) and n=18 (0.5%) and x (degree of polymerization)= 1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The water soluble nonionic surfactants which can be utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing 8 to 18 carbon atoms in a straight or branched chain configuration) condensed with 5 to 30 moles of ethylene oxide, for example, lauryl or myristyl alcohol condensed with 16 moles of ethylene oxide (EO), tridecanol condensed with 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to 14 carbon atoms in length and wherein the condensate contains either 6 moles of EO per mole of total alcohol or 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohols containing about 9–15 carbon atoms, such as $C_9$–$C_{11}$ alkanol condensed with 8 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of 8–15 and give good/W emulsification, whereas ethoxamers with HLB values below 8 contain less than 5 ethyleneoxy groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from 8 to 18 carbon atoms in a straight- or branched chain alkyl group with 5 to 30 moles of ethylene oxide. Specific examples of alkyl phenol ethoxylates include nonyl condensed with 9.5 moles of EO per mole of nonyl phenol, dinonyl phenol condensed with 12 moles of EO per mole of phenol, dinonyl phenol condensed with 15 moles of EO per mole of phenol and di-isoctylphenol condensed with 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1–3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being 75% by weight.

Other suitable water-soluble nonionic detergents which are less preferred are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L62 and L64.

The water-soluble zwitterionic surfactant, which can also be used provides good foaming properties and mildness to the present nonionic based liquid detergent. The zwitterionic surfactant is a water soluble betaine having the general formula:

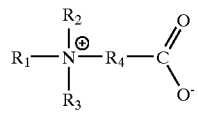

wherein $R_1$ is an alkyl group having 10 to 20 carbon atoms, preferably 12 to 16 carbon atoms, or the amido radical:

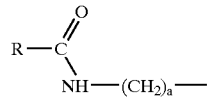

wherein R is an alkyl group having 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonio) acetate, myristyl dimethyl betaine, palmityl dimethyl betaine, lauryl diemethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine, distilled water); a specific gravity at 25° C. of 1.1 g/ml; a density at 25° C. of 9.1 lbs/gallon;

The cleaning composition contains at least one solubilizer selected from the group consisting of a $C_2$–$C_5$ mono, dihydroxy or polyhydroxy alkanols such as ethanol, isopropanol, glycerol, ethylene glycol, diethylene glycol, propylene glycol, and hexylene glycol and mixtures thereof, urea, and alkali metal salts of cumene, toluene or xylene sulfonates such as sodium cumene sulfonate and sodium xylene sulfonate and mixtures thereof.

The nanoparticles suspended in the instant composition are of zinc oxide. An especially preferred zinc Oxide particulate is manufactured by Sumitomo Osaka Cement (distributed by Maprecos) as Ultra fine zinc Oxide ZnO-350. Their appearance is white to pale yellow powder, with a particle size between 10 and 30 nm and a purity of at least 99.5%. As alternatives, other zinc Oxide particles of a size in the range of 5–350 nm may be used.

A viscosity building system or 3-D structuring agent may be optionally added at a concentration of 0.1 wt. % to 4 wt. % to the composition to help suspending the zinc oxide particulates. Among others, some potentially thickening systems can be selected in:—Polymers such as polyacrylates (linear or cross-linked), cellulose ethers (eg those derived from hydroxyethyl or hydroxypropyl cellulose), natural polysaccharides and gums (eg Carrageenan, Xanthan, etc) ;—Associative thickeners (eg hydrophobically modified modified polymers);—Inorganic thickeners (eg clay, laponite, etc)—Self thickened surfactant systems (eg containing alcohol ethoxy sulfates and/or betaines and/or amine oxides, etc., with or without salting out agent).

The magnesium inorganic salt which can be used in the instant composition are selected from the group consisting of magnesium oxide, magnesium chloride, and magnesium sulfate hepta hydrate and mixtures thereof.

The final essential ingredient in the inventive cleaning compositions is water. The proportion of water in the compositions generally is in the range of 35% to 90%, preferably 50% to 85% by weight of the cleaning composition.

The liquid cleaning composition of this invention may, if desired, also contain other components either to provide additional effect or to make the product more attractive to the consumer. The following are mentioned by way of example: Colors or dyes or perfumes in amounts up to 1.0% by weight; sodium bisulfite in amounts up to 0.2%, and pH adjusting agents, such as sulfuric acid or sodium hydroxide, as needed. Furthermore, if opaque compositions are desired, up to 4% by weight of an opacifier may be added. Other ingredients in amounts up to 5 wt. % are ethylene diamine tetraacefic acid sodium salt and hydroxy ethylene diamine tetraacetic acid sodium salt.

Preservatives can be optionally used in the instant compositions at a concentration of 0.005 wt. % to 3 wt. %, more preferably 0.01 wt. % to 2.5 wt. %. These preservatives are: benzalkonium chloride; formalin, benzethonium chloride, 5-bromo-5-nitro-1,3dioxane; 2-bromo-2-nitropropane-1,3-diol; alkyl trimethyl ammonium bromide; N-(hydroxymethyl)N-(1,3-dihydroxy methyl-2,5dioxo-4-imidaxolidinyl-N'-(hydroxy methyl)urea; 1-3-dimethyol-5,5-dimethyl hydantoin; formaldehyde; iodopropynl butyl carbamata, butyl paraben; ethyl paraben; methyl paraben; propyl paraben, mixture of methyl isothiazolinone/methylchloroisothiazoline in a 1:3 wt. ratio; mixture of phenoxythanol/butyl paraben/methyl paraben/propylparaben; 2-phenoxyethanol; tris-hydroxyethyl-hexahydrotriazine; methylisothiazolinone; 5-chloro-2-methyl4-isothiazolin-3-one; 1,2-dibromo-2,4-dicyanobutane; 1-(3-chloroalkyl)-3,5,7-triaza-azoniaadamantane chloride; and sodium benzoate.

The following example illustrates liquid cleaning composition of the described invention. Unless otherwise specified, all percentages are by weight. The exemplified composition is illustrative only and do not limit the scope of the invention. Unless otherwise specified, the proportions in the examples and elsewhere in the specification are by weight.

EXAMPLE I

The following reference composition in wt. % was prepared by simple mixing procedure. ZnO-350 is a white to pale yellow powder. The ZnO-350 powder is gently and homogeneously incorporated in the product at the end of the process.

|  | Example |
| --- | --- |
| Water | 10 |
| Linear alkyl benzene sulfonate Na salt | 3 |
| $NH_4$ $C_{13-14}$ AEOS 2:1 EO | 11.6 |
| Linear alkyl benzene sulfonate Mg salt | 9 |
| Lauryl myristylamido propyl dimethyl amine oxide | 5.5 |
| APG 625 | 10.0 |
| Zinc oxide-350 particulates | 0.1 |
| Water | Bal. |
| pH | 6.5–7.0 |
| Viscosity (Brookfield viscometer at 25C, spindle 5, 20 RPMS) cps | 4500 |

Such a composition remains clear and stable in the range of 15° C. to 35° C., especially 20° C. to 30° C. The liquid cleaning composition exhibits a viscosity around 4500 centipoise (cps) as measured at 25° C. with a Brookfield RVT Viscometer using a # 5 spindle rotating at 20 RPM.

The example demonstrates excellent skin compatibility that is much better than the same composition without the ZnO suspension, good foaming properties during hand washing, and good dish cleaning performance.

What is claimed:

1. A light duty liquid dishwashing composition with suspended nanoparticles of zinc oxide which comprises approximately by weight:

(a) 2% to 12% of an alkali metal or ammonium salt of a $C_{8-18}$ ethoxylated alkyl ether sulfate surfactant and/or a $C_{8-18}$ alkyl sulfate surfactant;

(b) 10% to 30% of an alkaline earth metal or alkali metal salt of an anionic $C_9$–$C_{18}$ alkyl benzene sulfonate surfactant;

(c) 0.5% to 10% of an alkyl polyglucoside surfactant;

(d) 0 to 10% of at least one solubilizer;

(e) 1% to 12% of an amine oxide;

(e) 0.01% to 1% of said solid nanoparticles of said zinc oxide of a particle size ranging between 10 and 30 nm;

(g) the balance being water.

2. The composition of claim 1, wherein said at least one solubilizer is selected from the group consisting of sodium, potassium, ammonium salts of cumene, xylene, toluene sulfonates, isopropanol, ethanol, glycerol, ethylene glycol, diethylene glycol and propylene glycol and mixtures thereof.

3. The composition of claim 1, wherein said solubilizer is sodium xylene sulfonate and ethanol.

4. The composition of claim 2, further including a magnesium inorganic acid.

5. A cleaning composition for all purpose cleaners, light duty liquids, shampoos such as hair cleaning, foam baths, liquid hand soaps, and shower gels which comprises approximately by weight:

(a) 1% to 50%, more preferably 2% to 40% of at least one surfactant selected from the group consisting of sulfonated anionic surfactants, sulfated anionic surfactants, zwitterionic surfactants, $C_{12}$–$C_{14}$ alkanol amide surfactants, amine oxide surfactants, ethoxylated nonionic surfactants, ethoxylated/propoxylated nonionic surfactants and alkyl polyglucoside surfactants and mixtures thereof;

(b) 0.5% to 10%, more preferably 1% to 8% of at least one solubilizer;

(c) 0.01% to 1%, more preferably 0.03% to 0.5% of Nano-particulates of zinc oxide which function as an anti-irritant system for the surfactants; and (d) the balance being water.

\* \* \* \* \*